United States Patent [19]

Fitzpatrick

[11] 4,192,799
[45] Mar. 11, 1980

[54] CONJUGATES FORMED BY REACTING A PROSTAGLANDIN MIMIC COMPOUND WITH A CARRIER MOLECULE

[75] Inventor: Francis A. Fitzpatrick, Kalamazoo, Mich.

[73] Assignee: The Upjohn Company, Kalamazoo, Mich.

[21] Appl. No.: 835,352

[22] Filed: Sep. 21, 1977

[51] Int. Cl.$^2$ .................... A61K 37/02; A61K 39/00
[52] U.S. Cl. .................... 260/121; 260/112 R; 260/112.5 R; 424/85
[58] Field of Search ............ 260/112 R, 121; 424/85

[56] References Cited

U.S. PATENT DOCUMENTS

| | | | |
|---|---|---|---|
| 3,867,366 | 2/1975 | Rubenstein et al. | 260/112 R X |
| 3,950,363 | 4/1976 | Bundy | 260/514 D X |
| 3,980,764 | 9/1976 | Adams | 260/112 R X |
| 4,041,076 | 8/1977 | Arenia et al. | 260/112 R X |
| 4,053,459 | 10/1977 | Christenson | 260/112 R X |

OTHER PUBLICATIONS

Corey et al, *Proc. Nat. Acad. Sci.*, vol. 72, No. 9, Sept. (1975), pp. 3355–3358.
Corey et al, *J.A.C.S.*, vol. 99, No. 6 (Mar. 1977), pp. 2006–2008.

*Primary Examiner*—Walter C. Danison
*Attorney, Agent, or Firm*—Martin B. Barancik

[57] ABSTRACT

A method for the radioimmunoassay of PGE$_1$-type and PGE$_2$-type compounds and PGX is disclosed which utilizes antibodies formed against a prostaglandin mimic.

Conjugates are disclosed which are formed by attaching a prostaglandin mimic to a carrier molecule.

Antibodies are disclosed which are specific against PGE$_1$-type and PGE$_2$-type compounds, PGH$_2$, and PGX.

Complexes are disclosed which are formed by binding an antibody raised against a prostaglandin mimic with its corresponding authentic prostaglandin.

18 Claims, No Drawings

CONJUGATES FORMED BY REACTING A PROSTAGLANDIN MIMIC COMPOUND WITH A CARRIER MOLECULE

BACKGROUND OF THE INVENTION

This invention is concerned with the problem of producing hapten-specific antibodies when the hapten is inherently unstable, as with $PGH_2$ and PGX, or when the hapten is changed during antibody production, as with certain PGE-type compounds. See, for example, Raz, et al., Eur. J. Biochem., 53, 145–150 (1975).

The specificity of the immune response is ancient knowledge; e.g., it was observed over the ages that persons who contracted smallpox, measles, etc. would not be reafflicted with the same disease but were not thereby protected from other diseases. The cross-reactivity of the immune response is also well known; e.g., the smallpox vaccine is derived from cowpox, not smallpox. The mechanism which creates antibodies which, although highly specific, may nevertheless cross-react with compounds other than the antigen which produced them is not fully understood. However, it is known that using substitutes which are merely gross space filling will not necessarily produce the desired antibodies. Thus, replacing the oxygen at C-9 in $PGE_1$ with chlorine yields a compound of the formula

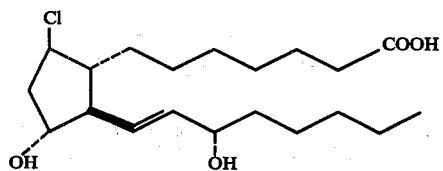

which does not produce antibodies specific against $PGE_1$. In developing an RIA for prostaglandins, Cornette, et al., Radioimmunoassay of Prostaglandins, The Prostaglandins, 243–255, Futura Pub. Co., N.Y., (1972), found little cross-reactivity between prostaglandins with different ring structures:". . . the specificity of the antibody is primarily determined by substituents on the cyclopentane ring . . ." (p. 247). See also: Salmon, Ng, and Karim, Prostaglandins, 9, 339–346 (1975).

Attempts have been made by different research groups to produce antibodies against $PGE_1$. The results of cross reaction experiments are summarized in Table I. In each example, rabbits were inoculated with a $PGE_1$ conjugate. The antibodies produced varied in selectivity. Relatively selective antibodies were produced in Example 1. Cross reaction with $PGE_2$ was only 20%. Moderately selective antibodies were produced in Examples 3, 5, and 7. Cross reaction with $PGE_2$ was about 50%. Non-selective antibodies were produced in Example 4. Cross reaction with $E_2$ or A and B series prostaglandins was 100%. In certain extreme cases, antibodies produced against $PGE_1$ conjugates showed greater selectivity to the B prostaglandins than to $PGE_1$ (Example 2), and in another example (6), the A series prostaglandins were also recognized preferentially even though a $PGE_1$ conjugate was used.

Similar results are seen in Table II from attempts to generate antibodies specific for $PGE_2$. The antibodies varied in selectivity. Relatively selective antibodies were obtained in Examples 1 and 4, where only $PGE_1$ crossreacted. In Example 2 an E-specific antibody was produced but there was no selectivity between $E_1$ and $E_2$. Again, extreme cases were observed as in Example 5, where prostaglandins $A_2$ and $B_2$ were recognized preferentially even though an $E_2$ conjugate was used. In Example 3, the A prostaglandins were recognized preferentially, although an $E_2$ conjugate was used.

Thus, cross-reaction is likely to be varied and unpredictable for some PG-type compounds.

Table 1

| Example | Conjugate | % Cross Reaction ||||||
|---|---|---|---|---|---|---|---|
| | | $PGE_1$ | $PGE_2$ | $PGA_1$ | $PGA_2$ | $PGB_1$ | $PGB_2$ |
| 1 | $PGE_1$-thyroglobulin[1] | 100 | 20 | — | — | — | — |
| 2 | $PGE_1$-poly-1-lysine[2] | 100 | 10 | 220 | 440 | 31,000 | 8,500 |
| 3 | $PGE_1$-porcine gamma globulin[3] | 100 | 50 | — | — | 10 | — |
| 4 | $PGE_1$-BSA[4] | 100 | 100 | 100 | 100 | — | 100 |
| 5 | $PGE_1$-BSA[4] | 100 | 40 | 25 | 10 | — | — |
| 6 | $PGE_1$-BSA[4] | 100 | 90 | 10,000 | 1000 | 100,000 | 50,000 |
| 7 | $PGE_1$-BSA[5] | 100 | 20 | 6 | — | 66 | — |

References:
[1]Ritzi and Stylos, Prostaglandins, 8, 55–66 (1974)
[2]Levine et al., J. Biol. Chem., 246, 6782–6785 (1974)
[3]Jubiz et al., Prostaglandins, 2, 471–489 (1972)
[4]Yu and Burke, Prostaglandins, 2, 11–22 (1972)
[5]Maclouf et al., FEBS Letters, 56, 273–278 (1975)

Table II

| Example | Conjugate | % Cross Reaction ||||||
|---|---|---|---|---|---|---|---|
| | | $PGE_2$ | $PGE_1$ | $PGA_2$ | $PGA_1$ | $PGB_2$ | $PGB_3$ |
| 1 | $PGE_2$-BSA[1] | 100 | 10 | 7 | 7 | 7 | 7 |
| 2 | $PGE_2$-KLH[2] | 100 | 110 | — | — | — | — |
| 3 | $PGE_2$-BSA[3] | 100 | 73 | 400 | 200 | — | 62 |
| 4 | $PGE_2$-hen gamma globulin[4] | 100 | 15 | 3 | — | — | — |
| 5 | $PGE_2$-BSA[5] | 100 | 55 | 550 | — | 580 | — |

References:
[1]Bauminger et al., Prostaglandins, 4, 313–324 (1973)
[2]Ritzi and Stylos Prostaglandins 8, 55-66 (1947)
[3]Zusman et al., Prostaglandins, 2, 41-53 (1972)
[4]Christensen and Leyssac, Prostaglandins, 11, 399–420 (1976)
[5]Raz et al., Eur. J. Biochem., 53, 145-150 (1975)

Performing radioimmunoassays (RIAs) for various of the PG-type compounds has been problematical primarily because of their instability. For example, $PGE_2$ dehydrates into $PGA_2$, which is further isomerized to PGB$_2$ during antibody production. The antibodies produced cross-react with PGA$_2$ and PGB$_2$ thereby interfering with the RIA for PGE$_2$.

As used herein, the term "prostaglandin" (or "PG") refers to those cyclopentane-containing carboxylic acids derived from mammalian tissues which are structural derivatives of prostanoic acid:

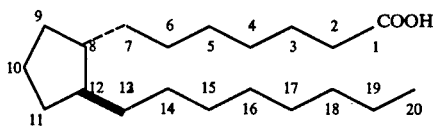

See Bergstrom, et al. Pharmacol. Rev. 20, 1 (1968) and references cited therein. For example, prostaglandin E$_2$ (PGE$_2$) has the following structure:

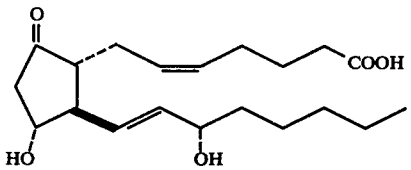

PGH$_2$ has the following structure:

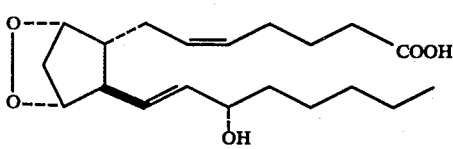

PGX (also known as prostacyclin, PGI$_2$, and 9-deoxy-6,9α-epoxy-Δ$^5$-PGF$_{1α}$) has the following structure:

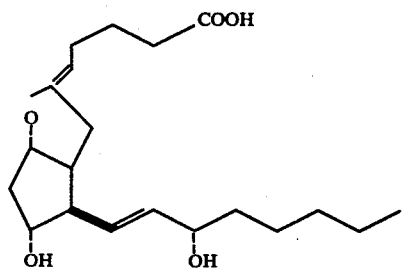

See also Nelson, Prostaglandin Nomenclature, J. of Med. Chem., 17, 911 (1974).

The term "prostaglandin analog" herein refers to those compounds structurally related to the prostaglandins (in that they exhibit a cyclopentane ring and a pair of side chains attached to adjacent carbon atoms of the ring) which retain certain characteristic biological properties of the prostaglandins. See Bergström, cited above. Various structural modifications of the prostaglandins are known to produce useful prostaglandin analogs. For example, the replacement of the carboxy with a hydroxymethyl is known, substitution of a methyl, ethyl, or fluoro for a hydrogen at, for example, C-16 is known. Further, partially deoxygenated prostaglandins are known to be useful prostaglandin analogs. Accordingly, 9-deoxy prostaglandins are known. Finally, there are known prostaglandin analogs wherein the double bonds of, for example, PGF$_{2α}$ are shifted, e.g., cis-4,5-didehydro-PGF$_{1α}$, or replaced by triple bonds, e.g., 13,14-didehydro-PGF$_{2α}$.

As used herein, the terms "PGE$_1$-type" and "PGE$_2$-type" compound refer to PGE$_1$, PGE$_2$, or their respective analogs of the formula

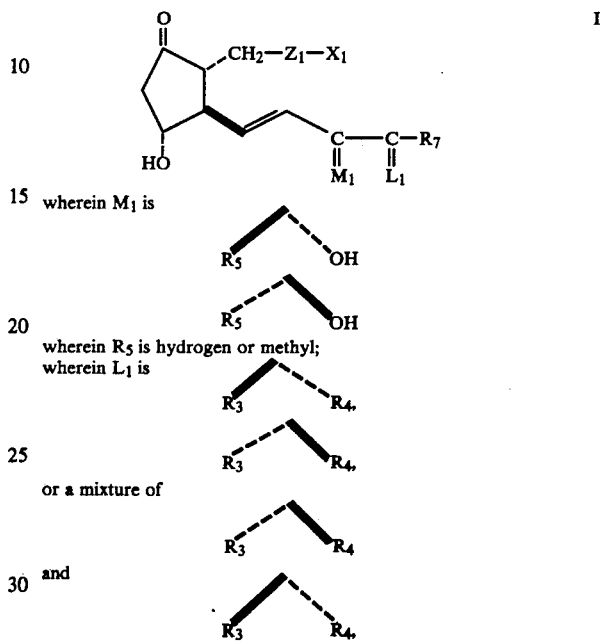

wherein M$_1$ is wherein R$_5$ is hydrogen or methyl;
wherein L$_1$ is or a mixture of and wherein R$_3$ and R$_4$ are hydrogen, methyl, or fluoro, being the same or different, with the proviso that one of R$_3$ and R$_4$ is fluoro only when the other is hydrogen or fluoro;

wherein Z$_1$ is
(1) cis—CH=CH—CH$_2$—(CH$_2$)$_g$—CH$_2$—,
(2) cis—CH=CH—CH$_2$—(CH$_2$)$_g$—CF$_2$—,
(3) cis—CH$_2$—CH=CH—(CH$_2$)$_g$—CH$_2$—,
(4) —(CH$_2$)$_3$—(CH$_2$)$_g$—CH$_2$—,
(5) —(CH$_2$)$_3$—(CH$_2$)$_g$—CF$_2$—,
(6) —CH$_2$—O—CH$_2$—(CH$_2$)$_g$—CH$_2$—,
(7) —C≡C—CH$_2$—(CH$_2$)$_g$—CH$_2$—,
(8) —CH$_2$—C≡C—(CH$_2$)$_g$—CH$_2$—,

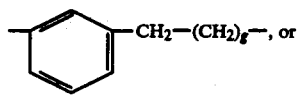 (9)

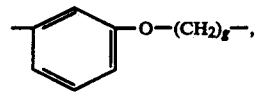 (10)

wherein g is one, 2, or 3;
wherein R$_7$ is

—(CH$_2$)$_m$—CH$_3$ (1)

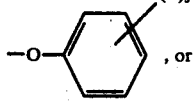 , or (2)

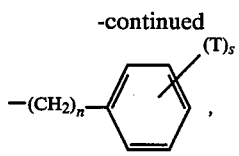

(3)

wherein m is one to 5, inclusive; n is zero or one; T is chloro, fluoro, trifluoromethyl, alkyl of one to 3 carbon atoms, inclusive, or alkoxy of one to 3 carbon atoms, inclusive; and s is zero, one, 2, or 3, the various T's being the same or different, with the proviso that not more than two T's are other than alkyl, with the further proviso that $R_7$ is

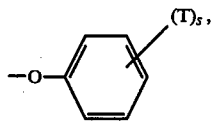

wherein T and s are as defined above, only when $R_3$ and $R_4$ are hydrogen or methyl, being the same or different; and wherein $X_1$ is $-COOR_1$ wherein $R_1$ is hydrogen or a pharmacologically acceptable cation.

"PGE-type" consists of $PGE_1$-type and $PGE_2$-type.

The terms "prostaglandin mimic" and "authentic prostaglandin" are used herein to differentiate between certain stable analogs and their corresponding prostaglandin-type compounds. These stable analogs (mimics) are characterized in that the antibodies formed against the analogs are highly cross-reactive (>30%) with the authentic prostaglandins. Specifically, the mimics to $PGE_1$- and $PGE_2$-type compounds are 9-deoxy-9-methylene PGF-type compounds having the ring structure

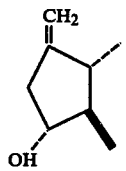

where the side chains are the same as shown in formula I. The mimic to $PGH_2$ is (5Z, 9α, 11α, 13E, 15S)-9,11-azo-15-hydroxyprosta-5,13-dien-1-oic acid:

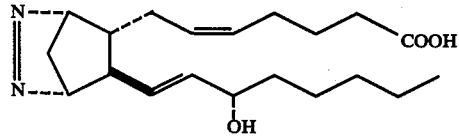

II

The mimic to PGX is 9-deoxy-6,9α-epoxy-$PGF_{1\alpha}$:

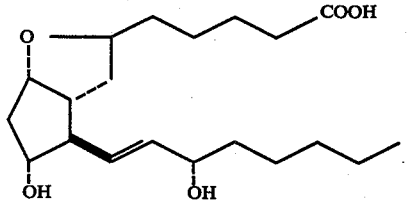

III

PGE-type compounds are known to be useful pharmacological agents capable of conventional formulations and administration by a wide variety of routes. See U.S. Pat. No. 3,903,297 for a description of typical methods of formulation and administration. See also Bergström, et al., cited above.

$PGH_2$, derived endogenously from arachidonic acid, is a transient regulator in mammalian cells. (See Hamberg and Samuelsson, Proc. Natn. Acad. Sci., U.S.A. 70, 889–903 (1973).) Upon formation, the endoperoxide is rapidly converted to $PGF_{2\alpha}$, $PGE_2$, their 15-keto-PG metabolites, and thromboxane $A_2$. (See Hamberg, et al., Proc. Natn. Acad. Sci., U.S.A. 72, 2994–2998 (1975) and Moncada, et al., Nature 263, 663–665 (1976).) The enzymatic composition of each tissue governs the nature and extent of these conversions. By its direct influence and as precursor for other PGs, $PGH_2$ is a primary cellular mediator; unfortunately, its short half-life makes direct determination of $PGH_2$-related phenomena difficult.

PGX is also endogenously formed from arachidonic acid. Of physiological significance is its potent opposition to the platelet aggregating properties of $PGH_2$ and thromboxane $A_2$, both of which have been implicated in the occurrence of thrombosis. (See Horton, Nature, 263, 627, (1976).) Like $PGH_2$, PGX is intrinsically unstable.

Radioimmunoassay (RIA) is a sensitive, analytical technique in which a compound to be measured and the same compound in a radioactive form compete for binding sites on antibodies showing a selective affinity for the compound. The discovery of the technique as it is used today is generally credited to Berson and Yalow, J. Clin. Invest., 38, 1996, (1959). The principles of radioimmunoassay determination have been described by Hawker, Radioimmunoassay and Related Methods, Anal. Chem., 45, 878A–888A, (1973), and Odell and Daughaday, Principles of Competitive Binding Assays, J. B. Lippincott, Phil., (1971). The method has been applied to the assay of numerous compounds.

A useful RIA method may be developed only when one has:

(1) The radiolabeled form of the compound to be measured (2) Antibodies with the ability to bind the compound to be measured. Ordinarily, the procurement of the radiolabeled form of the compound to be measured precedes the attempt to produce antibodies. The limiting step in the development of a radioimmunoassay method then is the successul production of antibodies with the ability to bind the compound to be measured.

Antibodies are plasma proteins synthesized in humoral immune responses which are capable of combining with the provoking antigens. There are several types of plasma proteins with associated antibody activity and these are denoted collectively as immunoglobulins. Antiserum is serum which contains antibodies.

Antigens (immunogens) are substances capable of provoking an immune response of any type in an immunologically competent vertebrate. Antigens are substances of high molecular weight (>2000), usually proteins or carbohydrates.

Haptens are incomplete antigens; i.e., substances by themselves incapable of provoking an immune response, but able to serve as partial immunogens when bound to another substance denoted as a carrier molecule. Haptens are usually of low molecular weight (<500) and may be of relatively simple structure. (See Sela (ed.), The Antigens, Academic Press, N.Y., 1973.)

Vertebrates stimulated (inoculated) by a conjugate (hapten-carrier molecule complex) will produce antibodies capable of reacting with the conjugate, the carrier molecule alone, and the hapten alone.

SUMMARY

This invention provides conjugates formed by coupling an appropriate PG mimic with a carrier molecule of high molecular weight. The conjugates are used to elicit antibodies.

The invention further provides antibodies extracted from a vertebrate after inoculation with these conjugates.

The antibodies have a variety of uses. As a purifying agent, an antibody can serve to selectively remove $PGE_2$ when the presence of $PGE_2$ in samples is undesirable. For example, when platelet rich plasma is incubated with the prostaglandin endoperoxide, $PGH_2$, both thromboxane $B_2$ ($TxB_2$) and $PGE_2$ are formed. The amount of $TxB_2$ is low, about 0.03–0.05 $\mu g$./per 1.0 $\mu g$. of $PGH_2$. The amount of $PGE_2$ is 50–100 times greater than the amount of $TxB_2$. Attempts to detect the $TxB_2$ by thin layer chromatography or gas chromatography are hampered by the presence of $PGE_2$ in excess of $TxB_2$. If the total $PGE_2$ and $TxB_2$ in the sample are extracted and the extracted residue is incubated with an excess of the mimic-PGE antiserum, the $PGE_2$ will be bound to the antibodies. If this antibody-$PGE_2$ complex is subsequently precipitated with ammonium sulfate and removed by centrifugation, the $TxB_2$ will remain in the supernatant. The $TxB_2$ in the supernatant may then be extracted and analyzed by thin layer chromatography or gas chromatography without interference from the $PGE_2$.

The detection of sub-nanogram levels of $PGE_2$ in biological samples is difficult because of the limited sensitivity of many assay techniques and the problems of interferences which are difficult to remove. For example, gas chromatography/mass-spectrometry requires approximately 50 nanograms of $PGE_2$ to obtain a usable mass spectrum. If a sample contained 0.5 ng. of $PGE_2$/ml. of sample, 100 ml. of sample could be extracted, and the residue would then contain 50 ng. of $PGE_2$. The extraction procedure is not selective, so the residue would likely contain considerable amounts of other prostaglandins, fatty acids, or extractable lipids which would interfere in the mass spectrometric measurements. Several additional chromatographic steps would be required before the sample was purified enough for mass spectrometry. Alternatively, the extracted residue described above could be incubated with sufficient mimic-PGE antibody to bind all of the $PGE_2$ present (50 ng.). The antibody-$PGE_2$ complex could be precipitated with ammonium sulfate and removed by centrifugation. All interfering materials would remain in the supernatant. The $PGE_2$ could be "stripped" from the antibody by a single additional extraction. In this case, the antibody serves as a means to enrich the $PGE_2$ content of an extracted sample relative to associated contamination from the extraction.

The invention further provides complexes formed by reacting an authentic prostaglandin with the antibodies raised against the corresponding PGE-type compound mimic, $PGH_2$ mimic, or PGX mimic. The complexes can be used as indicated in the above two examples and by extensions thereof or in an RIA.

The invention further provides a method of performing an RIA for PGE-type compounds and for PGX which comprises: (1) preparing a conjugate from a PG mimic and a carrier molecule, (2) inoculating a vertebrate with this conjugate, thereby stimulating antibody production, and (3) extracting antiserum produced in step 2 and diluting it to a concentration suitable for performing an RIA. Thus, by selecting the appropriate PG mimic, antibodies are produced which can be used to perform a highly specific RIA for the corresponding authentic prostaglandin.

PGE-type compounds are known pharmacologically active agents. This invention provides a useful tool to quantitatively and/or qualitatively assay for these useful compounds. Samples of biological tissue or fluid can be assayed. Thus, the assay can be used to measure PGE-type compound levels in the body following PGE-type compound administration or to determine the correlation between disease and levels of naturally occuring PGEs. For example, elevated PGE levels have been detected in patients with medullary carcinoma of the thyroid, and neuroblastoma. PGE levels in persons with Bartter's syndrome are higher than in persons with other kidney disorders.

The assay can also be used to measure the progress of the reaction used to synthesize PGE-type compounds. Thus, at predetermined intervals, samples can be extracted from the reaction vessel and quantitative assays made. The precise technique for any of these assays would depend on the data being sought or on the synthesis being run. It is expected that one of ordinary skill in this art would be able to make these determinations himself.

$PGH_2$ and PGX present particular problems because of their instability. For example, the half-life of $PGH_2$ in aqueous solution at room temperature is approximately five minutes. The novel antibodies of this invention can be used during $PGH_2$ or PGX biosysthesis to bind with these compounds as they are formed. This binding will sufficiently stabilize the compounds to allow for their isolation from the reaction vessel. At a later time, the $PGH_2$ or PGX can be stripped off the complex with aprotic organic solvents such as acetone or methylene chloride and purified. The ability to administer large quantitative amounts of $PGH_2$ and PGX is very useful in, for example, studies of the interrelationship of these very reactive compounds in thrombus formation. (See Moncada, et al., cited above.)

Since antibodies do not ordinarily penetrate the cell membrane, the antibodies of this invention may be used to discriminate between biological events which are regulated by $PGH_2$ intracellularly and those which are regulated by $PGH_2$ extracellularly. Likewide for PGX-regulated events.

DETAILED DESCRIPTION

Mimic Preparation

The mimics of this invention used for assaying PGE-type compounds are $PGF_1$-type and $PGF_2$-type compound of the formula

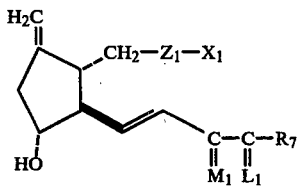

wherein M₁ is

or

wherein R₅ is hydrogen or methyl;
wherein L₁ is

or a mixture of

and

wherein R₃ and R₄ are hydrogen, methyl, or fluoro, being the same or different, with the proviso that one of R₃ and R₄ is fluoro only when the other is hydrogen or fluoro; wherein Z₁ is
(1) cis—CH=CH—CH₂—(CH₂)$_g$—CH₂—,
(2) cis—CH=CH—CH₂—(CH₂)$_g$—CF₂—,
(3) cis—CH₂—CH=CH—(CH₂)$_g$—CH₂—,
(4) —(CH₂)₃—(CH₂)$_g$—CH₂—,
(5) —(CH₂)₃—(CH₂)$_g$—CF₂—,
(6) —CH₂—O—CH₂—(CH₂)$_g$—CH₂—,
(7) —C≡C—CH₂—(CH₂)$_g$—CH₂—,
(8) —CH₂—C≡C—(CH₂)$_g$—CH₂—,

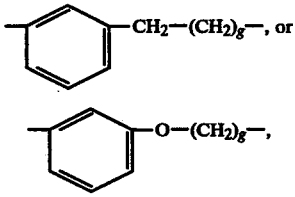

wherein g is one, 2, or 3;
wherein R₇ is

—(CH₂)$_m$—CH₃  (1)

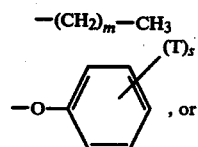  , or  (2)

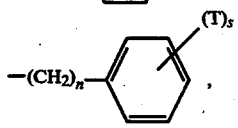  ,  (3)

wherein m is one to 5, inclusive, n is zero or one, T is chloro, fluoro, trifluoromethyl, alkyl of one to 3 carbon atoms, inclusive, or alkoxy of one to 3 carbon atoms, inclusive, and s is zero, one, 2, or 3, the various T's being the same or different, with the proviso that not more than two T's are other than alkyl, with the further proviso that R₇ is

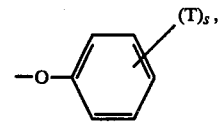

wherein T and s are as defined above, only when R₃ and R₄ are hydrogen or methyl, being the same or different; and
wherein X₁ is —COOR₁ wherein R₁ is hydrogen or a pharmacologically acceptable cation.

Preferably, the PGE-type compound mimics are compounds of the formula

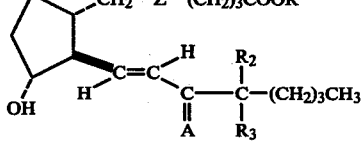

wherein Z is —CH₂CH₂— or cis—CH=CH—; wherein R is hydrogen or a pharmacologically acceptable cation; wherein R₂ and R₃ are hydrogen, methyl, or ethyl; and wherein A is

wherein R₄ is hydrogen, methyl, or ethyl with the proviso that R₂ and R₃ are both hydrogen when R₄ is methyl or ethyl.

Representative PGE-type compound mimics within the scope of this invention are shown in Table III.

TABLE III 1. 9-deoxy-9-methylene-PGF₂, sodium salt
2. 15-epi-9-deoxy-9-methylene-PGF₂
3. 13,14-didehydro-9-deoxy-9-methylene-PGF₂
4. 13,14-dihydro-9-deoxy-9-methylene-PGF₂
5. 2,2-difluoro-9-deoxy-9-methylene-PGF₂
6. 9-deoxy-9-methylene-PGF₁
7. 2,2-difluoro-9-deoxy-9-methylene-PGF₁
8. cis-4,5-didehydro-9-deoxy-9-methylene-PGF₁
9. 5,6-didehydro-9-deoxy-9-methylene-PGF₂
10. 4,4,5,5-tetradehydro-9-deoxy-9-methylene-PGF₁
11. 5-oxa-9-deoxy-9-methylene-PGF₁
12. 3,7-inter-m-phenylene-4,5,6-trinor-9-deoxy-9-methylene-PGF₁
13. 3,7-inter-m-phenylene-3-oxa-4,5,6-trinor-9-deoxy-9-methylene-PGF₁
14. 16-phenoxy-17,18,19,20-tetranor-9-deoxy-9-methylene-PGF₂
15. 17-phenyl-18,19,20-trinor-9-deoxy-9-methylene-PGF₂
16. 9-deoxy-9-methylene-2,2-difluoro-13,14-dihydro-PGF₂
17. 9-deoxy-9-methylene-2,2-difluoro-13,14-dihydro-PGF₁

18. 9-deoxy-9-methylene-cis-4,5-didehydro-13,14-dihydro-PGF$_1$
19. 9-deoxy-9-methylene-5-oxa-13,14-dihydro-PGF$_1$
20. 9-deoxy-9-methylene-5,6-didehydro-13,14-dihydro-PGF$_2$
21. 9-deoxy-9-methylene-4,4,5,5-tetradehydro-13,14-dihydro-PGF$_1$
22. 9-deoxy-9-methylene-15-epi-13,14-dihydro-PGF$_1$
23. 9-deoxy-9-methylene-2a,2b-dihomo-15-methyl-13,14-dihydro-PGF$_1$
24. 9-deoxy-9-methylene-2a,2b-dihomo-13,14-dihydro-PGF$_1$
25. 9-deoxy-9-methylene-16,16-dimethyl-13,14-dihydro-PGF$_1$
26. 9-deoxy-9-methylene-16,16-difluoro-13,14-dihydro-PGF$_1$
27. 9-deoxy-9-methylene-15-methyl-13,14-dihydro-PGF$_1$
28. 9-deoxy-9-methylene-13,14-dihydro-PGF$_1$
29. 9-deoxy-9-methylene-2a,2b-dihomo-15-epi-15-methyl-13,14-dihydro-PGF$_2$
30. 9-deoxy-9-methylene-2a,2b-dihomo-15-epi-13,14-dihydro-PGF$_2$
31. 9-deoxy-9-methylene-15-epi-16,16-dimethyl-13,14-dihydro-PGF$_2$
32. 9-deoxy-9-methylene-15-epi-16,16-difluoro-13,14-dihydro-PGF$_2$
33. 9-deoxy-9-methylene-15-epi-15-methyl-13,14-dihydro-PGF$_2$
34. 9-deoxy-9-methylene-2a,2b-dihomo-16,16-dimethyl-13,14-dihydro-PGF$_2$
35. 9-deoxy-9-methylene-2a,2b-dihomo-16,16-difluoro-13,14-dihydro-PGF$_2$
36. 9-deoxy-9-methylene-2a,2b-dihomo-15-methyl-13,14-dihydro-PGF$_2$
37. 9-deoxy-9-methylene-16,16-dimethyl-13,14-dihydro-PGF$_2$
38. 9-deoxy-9-methylene-16,16-dimethyl-13,14-dihydro-PGF$_2$
39. 9-deoxy-9-methylene-16,16-dimethyl-13,14-dihydro-PGF$_2$
40. 9-deoxy-9-methylene-15-methyl-16,16-difluoro-13,14-dihydro-PGF$_2$
41. 9-deoxy-9-methylene-16,16-difluoro-13,14-dihydro-PGF$_2$
42. 9-deoxy-9-methylene-15-methyl-13,14-dihydro-PGF$_2$, tris-(hydroxymethyl)aminomethane salt
43. 9-deoxy-9-methylene-15-methyl-13,14-dihydro-PGF$_2$
44. 9-deoxy-9-methylene-13,14-dihydro-PGF$_2$
45. 9-deoxy-9-methylene-2,2-difluoro-13,14-didehydro-PGF$_2$
46. 9-deoxy-9-methylene-2,2-difluoro-13,14-didehydro-PGF$_1$
47. 9-deoxy-9-methylene-cis-4,5-didehydro-13,14-didehydro-PGF$_1$
48. 9-deoxy-9-methylene-5-oxa-13,14-didehydro-PGF$_1$
49. 9-deoxy-9-methylene-5,6,13,14-tetradehydro-PGF$_2$
50. 9-deoxy-9-methylene-4,4,5,5,13,14-hexadehydro-PGF$_1$
51. 9-deoxy-9-methylene-15-epi-13,14-didehydro-PGF$_1$
52. 9-deoxy-9-methylene-2a,2b-dihomo-15-methyl-13,14-didehydro-PGF$_1$
53. 9-deoxy-9-methylene-2a,2b-dihomo-13,14-didehydro-PGF$_1$
54. 9-deoxy-9-methylene-16,16-dimethyl-13,14-didehydro-PGF$_1$
55. 9-deoxy-9-methylene-16,16-difluoro-13,14-didehydro-PGF$_1$
56. 9-deoxy-9-methylene-15-methyl-13,14-didehydro-PGF$_1$
57. 9-deoxy-9-methylene-13,14-didehydro-PGF$_1$
58. 9-deoxy-9-methylene-2a,2b-dihomo-15-epi-15-methyl-13,14-didehydro-PGF$_2$
59. 9-deoxy-9-methylene-2a,2b-dihomo-15-epi-13,14-didehydro-PGF$_2$
60. 9-deoxy-9-methylene-15-epi-16,16-methyl-13,14-didehydro-PGF$_2$
61. 9-deoxy-9-methylene-15-epi-16,16-difluoro-13,14-didehydro-PGF$_2$
62. 9-deoxy-9-methylene-15-epi-15methyl-13,14-didehydro-PGF$_2$
63. 9-deoxy-9-methylene-2a,2b-dihomo-16,16-dimethyl-13,14-didehydro-PGF$_2$
64. 9-deoxy-9-methylene-2a,2b-dihomo-16,16-difluoro-13,14-didehydro-PGF$_2$
65. 9-deoxy-9-methylene-2a,2b-dihomo-15-methyl-13,14-didehydro-PGF$_2$
66. 9-deoxy-9-methylene-16,16-dimethyl-13,14-didehydro-PGF$_2$, tris(hydroxymethyl)aminomethane salt
67. 9-deoxy-9-methylene-16,16-dimethyl-13,14-didehydro-PGF$_2$
68. 9-deoxy-9-methylene-15-methyl-16,16-difluoro-13,14-didehydro-PGF$_2$
69. 9-deoxy-9-methylene-16,16-difluoro-13,14-didehydro-PGF$_2$
70. 9-deoxy-9-methylene-15-methyl-13,14-didehydro-PGF$_2$, tris(hydroxymethyl)aminomethane salt
71. 9-deoxy-9-methylene-15-methyl-13,14-didehydro-PGF$_2$
72. 9-deoxy-9-methylene-13,14-didehydro-PGF$_2$
73. 9-deoxy-9-methylene-16,16-difluoro-PGF$_2$
74. 9-deoxy-9-methylene-cis-4,5-didehydro-PGF$_1$
75. 9-deoxy-9-methylene-15-methyl-PGF$_2$
76. 9-deoxy-9-methylene-5,6-didehydro-PGF$_2$
77. 9-deoxy-9-methylene-15-epi-PGF$_1$
78. 9-deoxy-9-methylene-2a,2b-dihomo-15-methyl-PGF$_1$
79. 9-deoxy-9-methylene-2a,2b-dihomo-PGF$_1$
80. 9-deoxy-9-methylene-16,16-dimethyl-PGF$_1$
81. 9-deoxy-9-methylene-16,16-difluoro-PGF$_1$
82. 9-deoxy-9-methylene-15-methyl-PGF$_1$,
83. 9-deoxy-9-methylene-PGF$_2$
84. 9-deoxy-9-methylene-2a,2b-dihomo-15-epi-15-methyl-PGF$_2$
85. 9-deoxy-9-methylene-2a,2b-dihomo-15-epi-PGF$_2$
86. 9-deoxy-9-methylene-15-epi-16,16-dimethyl-PGF$_2$
87. 9-deoxy-9-methylene-15-epi-16,16-difluoro-PGF$_2$
88. 9-deoxy-9-methylene-15-epi-15-methyl-PGF$_2$
89. 9-deoxy-9-methylene-2a,2b-dihomo-16,16-dimethyl-PGF$_2$
90. 9-deoxy-9-methylene-2a,2b-dihomo-16,16-difluoro-PGF$_2$
91. 9-deoxy-9-methylene-2a,2b-dihomo-15-methyl-PGF$_2$ 92. 9-deoxy-9-methylene-16,16-dimethyl-PGF$_2$, tris(hydroxymethyl)aminomethane salt
93. 9-deoxy-9-methylene-16,16-dimethyl-PGF$_2$,
94. 9-deoxy-9-methylene-15-methyl-16,16-difluoro-PGF$_2$
95. 9-deoxy-9-methylene-15-methyl-PGF$_2$ tris(hydroxymethyl)aminomethane salt The PGE-type compound mimics of this invention are either known or can be prepared by one or ordinary skill in the art according to the method shown in U.S. Pat. No. 3,950,363, issued Apr. 13, 1976, or by obvious modifications thereto. According to this method, the following compounds can be made:
9-deoxy-9-methylene PGF$_1$-type compounds
9-deoxy-9-methylene-PGF$_1$
9-deoxy-9-methylene PGF$_2$-type compounds
9-deoxy-9-methylene-PGF$_2$
9-deoxy-9-methylene-15(R)-15-methyl-PGF$_2$
9-deoxy-9-methylene-15(S)-15-methyl-PGF$_2$ In order to maximize the specificity of the antibodies, a PGF-type compound would be chosen that would most closely approximate the PGE-type compound to be tested. So, 9-deoxy-9-methylene-15(R)-15-methyl-PGF$_2$ would be the hapten of choice to raise the antibodies to bind 15(R)-15-methyl PGE$_2$. Thus, 15(R)-15-methyl-PGE$_2$ is the "corresponding authentic prostaglandin" of 9-deoxy-9-methylene-15(R)-15-methyl-PGF$_2$.

The mimic of this invention used for PGH$_2$ is (5Z, 9$\alpha$, 11$\alpha$, 13E, 15S)-9,11-azo-15-hydroxyprosta-5,13-dien-1-oic acid, formula II, which is prepared by the method of Corey et al., Proc. Nat'l. Acad. Sci., USA, 72, 3355–3358 (1975).

The mimic of this invention used for assaying PGX is 9-deoxy-6,9$\alpha$-epoxy-PGF$_{1\alpha}$, formula III, which is prepared by the method of Corey et al., Jour. of Amer. Chem. Soc., 99, 2006–8 (1977).

Conjugate Preparation

A conjugate capable of evoking an immunogenic response is prepared by attaching a PG mimic to a natural protein, synthetic polypeptide, or other macromolecular immunogen (2000< mol. wt. <500,000) preferably containing available amine groups. Ordinarily this is done by activating the PG mimic's carboxyl group, then reacting the activated carboxyl group with amine groups on the immunogen. Many procedures are suitable including activation with carbonyl diimidazole, alkylchloroformate where the alkyl is of one through eight carbon atoms, or carbodiimide. Other methods of forming bonds between carboxylic acids and immunogens may be suitable. The preferred procedure uses water soluble carbodiimide, 1-ethyl-3-(3-dimethylaminopropyl)carbodiimide. Numerous natural proteins, synthetic polypeptides, and other immunogenic macromolecules have been used to elicit antibodies against haptens. Typical among these are keyhole limpet hemocyanin (KLH), albumins and globulins from different species including hen, rabbit, pig, goat, sheep, horse, cow, and man, and poly-1-lysine or other polypeptides of constant or variable amino acid sequences with molecular weight in excess of 2000. A preferred immunogen is KLH. An immunogen of nearly equal preferance is bovine serum albumin (BSA). The procedure of preparing a prostaglandin mimic conjugate is illustrated below.

In preparations 1 through 9 below, the use of 1 μl. of radioactive tracer as part of the original reactants allows one to make a quantitative measurement of the yield. Yields of >10% are preferred for the inoculation process. Typical yields range from 15% to 30%. In all cases, after preparation, the conjugate should be stored in a dessicator at −20° C.

All temperatures are in degrees Centigrade.

Preparaton 1: KLH-PGE$_2$ Mimic Conjugate

Ten mg. 9-deoxy-9-methylene-PGF$_2$ is dissolved in 2 ml. of dimethylformamide. Twenty mg. of KLH and 10 mg. of 1-ethyl-3-(3-dimethylaminopropyl)carbodiimide.HCl are mixed in 6.0 ml. of distilled water and the pH is adjusted to 7.0±0.5. The dimethylformamide solution containing the PGE$_2$ mimic is added dropwise, while the pH is maintained at 7.0±0.5. After reaction at 25°±10° for 1 hour. an additional 10 mg. of 1-ethyl-3-(3-dimethylaminopropyl) carbodiimide is added. The mixture is allowed to stand for 12 hours at 25°±10°, then the contents of the reaction vessel are dialyzed against 4 liters of distilled water for 24 hours to remove unreacted prostaglandin mimic, excess carbodiimide, or low molecular weight reaction side products. After dialysis, the contents of the dialysis membrane are lyophilized. The solid protein recovered containing prostaglandin mimic attached to the original protein via amide bonds is the KLH-PGE$_2$ mimic. The yield is 25.5%.

In a similar manner, other PGE-type mimic-KLH conjugates can be formed by substituting the appropriate 9-deoxy-9-methylene PGF-type compound of formula IV such as one of those in Table III for 9-deoxy-9-methylene PGF$_2$ in the procedure above.

Preparation 2: KLH-15(R)-15-Methyl-PGE$_2$ Mimic Conjugate

Following the procedure of preparation 1 but substituting 9-deoxy-9-methylene-15(R)-15-methyl-PGF$_2$ for 9-deoxy-9-methylene-PGF$_2$, KLH-15(R)-15-methyl-PGE$_2$ mimic conjugate is formed. The yield is 16.3%

Preparation 3: KLH-15(S)-15-Methyl-PGE$_2$ Mimic Conjugate

Following the procedure of preparation 1 but substituting 9-deoxy-9-methylene-15(S)-15-methyl-PGF$_2$ for 9-deoxy-9-methylene-PGF$_2$, KLH-15(S)-15-methyl-PGE$_2$ mimic conjugate is formed.

Preparation 4: BSA-PGE$_2$ Mimic Conjugate

Ten mg. of 9-deoxy-9-methylene PGF$_2$ is dissolved in 2 ml. of dimethylformamide. Twenty mg. of BSA and 10 mg. of 1-ethyl-3-(3-dimethylaminopropyl)carbodiimide.HCl are mixed in 6 ml. of distilled water, and the pH is adjusted to 5.5±0.5. The dimethylformamide solution containing the PGE$_2$ mimic is added dropwise with stirring while the pH is maintained at 5.5±0.5 for 1 hour at 25°±10°. The mixture is then allowed to stand for 12 hours at 25°±10°. The reaction products are dialyzed and lyophilized as before to yield BSA-PGE$_2$ mimic conjugate. The yield is 17.5%.

In a similar manner, other PGE-type mimic-BSA conjugates can be formed by substituting the appropriate 9-deoxy-9-methylene PGF compound of formula IV such as one of those in Table III for 9-deoxy-9-methylene PGF$_2$ in the above procedure.

Preparation 5: BSA-15(R)-15-Methyl-PGE$_2$ Mimic Conjugate

Following the procedure of preparation 4 but substituting 9-deoxy-9-methylene-15(R)-15-methyl-PGF$_2$ for 9-deoxy-9-methylene-PGF$_2$, BSA-15(R)-15-methyl-PGE$_2$ mimic conjugate is formed. The yield is 15.5%.

Preparation 6: KLH-PGH$_2$ Mimic Conjugate

Ten mg. of (5Z,9α,11α,13E,15S)-9,11-azo-15-hydroxyprosta-5,13-dien-1-oic acid is dissolved in 2 ml. of dimethylformamide. Twenty mg. of KLH and 10 mg. of 1-ethyl-3-(3-dimethylaminopropyl)carbodiimide.HCl are mixed in 6.0 ml. of distilled water and the pH is adjusted to 7.0±0.5. The dimethylformamide solution containing the PGH$_2$ mimic is added dropwise, with stirring, while the pH is maintained at 7.0±0.5. After reaction at 25°±10° for 1 hour, an additional 10 mg. of 1-ethyl-3-(3-dimethylaminopropyl)carbodiimide is added. The mixture is allowed to stand for 12 hours at 25°±10°, then the contents of the reaction vessel are dialyzed against 4 liters of distilled water for 24 hours to remove unreacted prostaglandin mimic, excess carbodiimide, or low molecular weight reaction side products. After dialysis, the contents of the dialysis membrane are lyophilized. The solid protein recovered containing prostaglandin mimic attached to the original protein via amide bonds is the KLH-PGH$_2$ mimic conjugate. The yield is 16.3%.

Preparation 7: BSA-PGH$_2$ Mimic Conjugate

Ten mg. of (5Z,9α,11α,13E,15S)-9,11-azo-15-hydroxyprosta-5,13-dien-1-oic acid is dissolved in 2 ml. of dimethylformamide. Twenty mg. of BSA and 10 mg. of 1-ethyl-3-(3-dimethylaminopropyl)carbodiimide.HCl are mixed in 6 ml. of distilled water, and the pH is adjusted to 5.5±0.5. The dimethylformamide solution containing the PGH$_2$ mimic is added dropwise with stirring while the pH is maintained at 5.5±0.5 for 1 hour at 25°±10°. The mixture is then allowed to stand for 12 hours at 25°±10°. The reaction products are dialyzed and lyophilized as before to yield BSA-PGH$_2$ mimic conjugate. The yield is 20.0%.

Preparation 8: KLH-PGX Mimic Conjugate

Ten mg. of 9-deoxy-6,9α-epoxy-PGF$_{1α}$ is dissolved in 2 ml. of dimethylformamide. Twenty mg. of KLH and 10 mg. of 1-ethyl-3-(3-dimethylaminopropyl)carbodiimide.HCl are mixed in 6.0 ml. of distilled water and the pH is adjusted to 7.0±0.5. The dimethylformamide solution containing the PGX mimic is added dropwise, with stirring, while the pH is maintained at 7.0±0.5. After reaction at 25°±10° for 1 hour, an additional 10 mg. of 1-ethyl-3-(3-dimethylaminopropyl)carbodiimide is added. The mixture is allowed to stand for 12 hours at 25°±10°, then the contents of the reaction vessel are dialyzed against 4 liters of distilled water for 24 hours to remove unreacted prostaglandin mimic, excess carbodiimide, or low molecular weight reaction side products. After dialysis, the contents of the dialysis membrane are lyophilized. The solid protein recovered containing prostaglandin mimic attached to the original protein via amide bonds is the KLH-PGX mimic conjugate. The yield is 17.3% grams.

Preparation 9: BSA-PGX Mimic Conjugate

Ten mg. of 9-deoxy-6,9α-epoxy-PGF$_{1α}$ is dissolved in 2 ml. of dimethylformamide. Twenty mg. of BSA and 10 ml. of 1-ethyl-3-(3-dimethylaminopropyl)carbodiimide.HCl are mixed in 6 ml. of distilled water, and the pH is adjusted to 5.5±0.5. The dimethylformamide solution containing the PGX mimic is added dropwise with stirring while the pH is maintained at 5.5±0.5 for 1 hour at 25°±10° C. The mixture is then allowed to stand for 12 hours at 25°±10°. The reaction products are dialyzed and lyophilized as befor to yield BSA-PGX mimic conjugate. The yield is 20.2%.

Production of Antibodies

Antibodies which will bind the prostaglandin mimic and its authentic counterpart are developed in animals following exposure to conjugates of the type prepared as shown above. Suitable animal species include guinea pig, rabbit, goat, pig, hen, cow, sheep, and horse. Animals of either sex are suitable.

Exposure to conjugate is accomplished by intramuscular, intradermal, intravenous, or subcutaneous administration. When subcutaneous or intradermal administration is used, the conjugate is injected at 20-40 sites on the animal flanks. Other routes of administration are suitable.

Doses vary depending on the particular animal species and individual animal sensitivity. Doses of 0.5-10 mg. conjugate/kg. animal weight are typical for primary inoculation. Booster injections require less conjugate, depending on the hypersensitivity of the individual animal. Doses of 0.5-0.1× the primary dose are typical for booster injections.

Primary inoculation is done with a complete adjuvant such as Freund's complete adjuvant to amplify the immune response. Booster injections are ordinarily made with incomplete adjuvant, such as Freund's incomplete adjuvant. The conjugate is prepared for inoculation by adding to it the adjuvant and a 0.9% saline solution and mixing all these in a high-speed blender until the mixture approaches the consistency of meringue.

On the same day as the inoculation with the conjugate, the animal is injected with 0.5 ml./kg. of attenuated pertussis vaccine intramuscularly. The purpose of this is to amplify the animal's immune response. This is done only with the primary inoculation.

Booster injections are made 20-50 days following the primary inoculation.

Two weeks following the booster injection and at weekly intervals thereafter, the animals are bled and their serum tested. Serum against a PGE-type mimic can be regarded for further study when at a minimum dilution of about 1:100 it binds at least 25% of the radiolabeled form of the authentic PG corresponding to the hapten used to elicit the antibodies. It is preferred that the binding be at least 50±3% at a dilution of 1:100. If animals do not reach the 50% level of response 30-60 days following the booster, they should be boosted again. It is preferred that animals showing this level of response not be boosted again until the titer of their antiserum shows a decline. They should then be boosted with approximately 0.5-0.25× the dose of the first boost.

In the case of PGH$_2$ and PGX an indirect measurement is used in which the presence of antibodies is detected by the opposition of the antiserum to the normal pharmacological response of PGH$_2$ or PGX. For example, since PGH$_2$ aggregates platelets, the extent of the ability of the antiserum to prevent aggregation in plasma exposed to PGH$_2$ is a function of the amount of PGH$_2$-specific antibodies in the antiserum. PGX inhibits the aggregation of platelet rich plasma (PRP) by arachidonic acid or PGH$_2$. The extent of the ability of antiserum to prevent this inhibition is a function of the concentration of antibodies specific against PGX.

The titer of PGH$_2$ mimic antiserum is sufficient when 100 μl. of undiluted antiserum delays platelet aggregation (1.0 ml. platelet rich plasma; 400 μg. arachidonic acid) for 1±0.1 minute at the midpoint of the maxium aggregatory response. It is preferred that the delay be at least 1±0.1 minute when no more than 50 μl. of undiluted antiserum is used. The amount of PGH$_2$ produced during these aggregations is sufficiently large that it is preferred to use the antiserum undiluted. It is understood that the procedure described is, in fact, the method for assigning the antiserum titer and in cases where exceptionally high titered antiserum is produced preliminary dilution of the antiserum may be needed.

The titer of PGX mimic antiserum is sufficient when 50 μl. of undiluted antiserum restores the platelet aggregation (2.0 ml. platelet rich plasma; 1000 μg. arachidonic acid) which was blocked by 0.050 μg. of PGX in less than 10±1 minutes. It is preferred that no more than 30 μl. of the PGX antiserum restore the platelet aggregation. It is preferred to use the antiserum undiluted although it is understood that the procedure described is, in fact, the method for assigning the antiserum titer and in cases where exceptionally high titered antiserum is produced, a preliminary dilution of the antiserum may be needed.

An alternative, although less desirable method of reboosting, is to schedule re-boosting for every 8–10 weeks after the serum has reached the critical levels described above.

Representative procedures for the production of antibodies are shown below. Since the production of antibodies varies from species to species and even from individual to individual, it should be understood that these procedures are only representative and not a limitation on the invention. Individual differences and situations will require that the practitioner vary the procedure to fit his particular circumstances.

Procedure 1: KLH-PGE$_2$ Mimic Antibodies

Five milligrams of KLH-PGE$_2$ mimic conjugate is added to 2.25 ml. of sterile saline (0.9%) and 2.25 ml. of Freund's complete adjuvant and blended. 1.0 ml. of this mixture is injected subcutaneously at 20–30 sites on the flanks of four Albino New Zealand rabbits of 2–4 kg. mass. Each rabbit receives a dose of about 1 mg. On the same day, 1.0 ml. of attenuated pertussis vaccine is injected intramuscularly at four sites on the hindquarters of each rabbit.

About 50 days following the primary inoculation, the animals are boosted with the following preparation:
2.5 mg. of KLH-PGE$_2$ mimic conjugate, 2.25 ml. of sterile saline (0.9%) and 2.25 ml. of Freund's incomplete adjuvant or equivalent, blended as before.
Each rabbit receives a dose of about 500 μg., injected as before. Antiserum is collected when the critical levels described above are reached.

Antibodies against other PG mimics can be elicited by substituting equal amounts of other conjugates, such as those of preparations 1 through 9, for the KLH-PGE$_2$ mimic conjugate in procedure 1. For example, the following conjugates can be substituted:

| Mimic of | Carrier Molecule | |
|---|---|---|
| | KLH | BSA |
| 1. PGE$_1$ | X | X |
| 2. PGE$_2$ | — | X |
| 3. 15(R)-15-methyl-PGE$_2$ | X | X |
| 4. 15(S)-15-methyl-PGE$_2$ | X | X |
| 5. PGH$_2$ | X | X |
| 6. PGX | X | X |

Procedure 2: BSA-PGH$_2$ Mimic Antibodies 1.0 mg. of BSA-PGH$_2$ mimic conjugate is added to 1.0 ml. of sterile saline (0.9%) and 1.0 ml. of Freund's complete adjuvant and blended. This mixture is injected intradermally at 30–40 sites on the flanks of an Albino New Zealand rabbit, which is also injected with 1.0 ml. of attenuated pertussis vaccine at four sites on the hindquarters. A total of two rabbits are inoculated in this manner.

Booster injections prepared as above but 0.2× the primary dose are administered four weeks after the first inoculation and at 7–10 week intervals thereafter. The animals are bled 2–3 weeks following each boosting.

Antibodies against other PG mimics can be elicited by substituting equal amounts of other conjugates for the BSA-PGH$_2$ mimic conjugate in procedure 2. For example, the following conjugates can be substituted:

| Mimic of | Carrier Molecule | |
|---|---|---|
| | KLH | BSA |
| 1. PGH$_2$ | X | — |
| 2. PGX | X | X |

Measurement of Titer

The titer of antibodies raised against the PGE-type mimics is obtained as follows. Antiserum is diluted to various concentrations (e.g., 1:100, 1:500, 1:1000, 1:5000) with 0.1 M phosphate buffered saline (0.9%) at pH 7.4, containing 0.1% gelatin, hereinafter 0.1 M PBSG. A radio-labeled form (10,000 cpm/0.2 ml. of 0.1 M PBSG) of the authentic PG corresponding to the mimic used to raise the antibodies and 0.1 ml. of each antiserum dilution are incubated at 25°±10° for one hour, then at 4°±3° for 12–16 hours. The antibody bound and free fractions are separated by adsorption with dextran-coated charcoal as described by Kahn, Andrieu, and Dray, Immunochemistry, 11, 327–332, (1974).

Variations of this exact procedure may be suitable. For example, buffers other than 0.1 M PBSG may be used. Any standard technique such as double antibody, ammonium sulfate, or polyethylene glycol precipitation may be suitable for separating antibody bound and free fractions. (See Hawker, cited above).

Tritiated PG-type compounds, e.g. [$^3$H] PGE$_2$, are desirable as tracers. They can be obtained from New England Nuclear (Boston, Mass.) or Amersham Searle (Oak Park, Ill.) or [$^3$H] arachidonic acid can be purchased from these sources for biosynthetic preparation (Wallach and Daniels, Biochimica Biophysica Acta 231, 445–457 (1971)) or they can be synthesized totally (Corey et. al., J. Am. Chem. Soc. 92, 397 (1970)).

Procedure 3: Titer of KLH-PGE$_2$ Mimic Antibodies

Using antiserum collected according to procedure 1, dilution of 1:100, 1:200, 1:500, 1:1000, 1:3000, 1:4000, and 1:6000 are prepared using 0.1 M PBSG. 0.2 ml. of [$^3$H]PGE$_2$ in 0.1 M PBSG and 0.1 ml. of each dilution of antiserum are incubated at 25°±10° for one hour, then at 4°±3° for 12–16 hours. The antibody bound and free portions are separated and the following data are obtained:

| Antiserum Dilution | % Bound (± 3%) |
|---|---|
| 1:100* | 59% |
| 1:200* | 59% |
| 1:500* | 48% |
| 1:1000 | 38% |
| 1:2000 | 23% |
| 1:3000 | 17% |
| 1:4000 | 13% |
| 1:6000 | 8% |

*Dilutions of 1:500 or less are desirable.

Using this procedure titers can be run for the other KLH-PGE-type mimic antisera collected according to procedure 1.

Procedure 4: Titer of BSA-PGE$_2$ Mimic Antibodies

Using antiserum collected according to procedure 1, dilutions of 1:100, 1:200, 1:500, 1:1000, and 1:2000 are prepared using 0.1 M PBSG. 0.2 ml. of [$^3$H]PGE$_2$ in 0.1 M PBSG and 0.1 ml. of each dilution of antiserum are incubated and separated as in procedure 3 and the following data are obtained:

| Antiserum Dilution | % Bound (± 3%) |
|---|---|
| 1:100* | 49% |
| 1:200 | 43% |
| 1:500 | 33% |
| 1:1000 | 26% |
| 1:2000 | 19% |

*Desirable dilution

Using this procedure titers can be run for the other BSA-PGE-type mimic antisera collected according to procedure 1.

Procedure 5: Titer of KLH-15(R)-15-methyl-PGE$_2$ Mimic Antibodies

Using antiserum collected according to procedure 1, dilutions of 1:100, 1:500, 1:1000, and 1:5000 are prepared using 0.1 M PBSG. 0.2 ml. of [$^{125}$I] 15(R)-15-methyl-PGE$_2$ histamide (10,000 cpm/0.1 ml.) in 0.1 M PBSG and 0.1 ml. of each dilution of antiserum are incubated and separated as in procedure 3 and the following data are obtained:

| Antiserum Dilution | % Bound (± 3%) |
|---|---|
| 1:100* | 71.3 |
| 1:500* | 67.1 |
| 1:1000* | 60.2 |
| 1:5000 | 31.1 |

*Dilutions of 1:1000 or less are desirable.

An alternative method of determining if sufficient antibodies are being formed is the indirect method of measuring the effects of the antibodies on the activity of the authentic prostaglandins.

Procedure 6: Titer of KLH-PGX Mimic Antibodies

PRP is prepared by centrifuging fresh, human blood collected over citrate (1 part 3.8% citrate/10 parts blood) at 200 g's for 10 minutes at 25°. Two ml. of PRP containing either normal rabbit serum or 9-deoxy-6,9α-epoxy-PGF$_{1\alpha}$ antiserum in the amounts shown below are incubated at 37° C. for 2 minutes, then transferred to an aggregometer cuvette containing 1 mg. of arachidonic acid and 0.050 μg. PGX (except for the 100% control, when no PGX is used). The PRP is stirred at 1100 rpm at 37° while the ensuing aggregation is monitored on a Payton aggregometer. The restoration of the aggregation is expressed as the $t_{50}$, i.e., the time at which 50% of maximal aggregation response occurs. Increasing amounts of antiserum restore the $t_{50}$ from total inhibition ($t_{50} = \infty$) to approximately the control value ($t_{50} = 1$ minute) in a concentration-dependent fashion.

| Amount of Serum | Arachidonic Acid | PGX (μg) | $t_{50}$ (min) |
|---|---|---|---|
| 100 μl. Normal Rabbit Serum (100% Control) | 1 mg. | 0 | 1.0 |
| 100 μl. PGX Mimic Antiserum | 1 mg. | 0.050 | 1.73 |
| 50 μl. PGX Mimic Antiserum | 1 mg | 0.050 | 2.30 |
| 30 μl. PGX Mimic Antiserum | 1 mg. | 0.050 | 6.50 |
| 100 μl. Normal Rabbit Serum (0% Control) | 1 mg. | 0.050 | ∞ |

The method of procedure 6 may also be used to measure the titer of BSA-PGX mimic antibodies.

Procedure 7: Titer for BSA-PGH$_2$ Mimic Antibodies

To run a titer for PGH$_2$, PRP is prepared as above. The influence of PGH$_2$ mimic antiserum is determined by incubating 2 ml. of PRP containing either 50–200 μl. of normal rabbit serum or 50–200 μl. of PGH$_2$ mimic antiserum for 2 minutes at 37°. The PRP is transferred to a cuvette containing 400 μg./ml. of arachidonic acid. The aggregation is monitored on a Payton aggregometer and the following data are obtained:

| Vol. of Antiserum | Delay of Aggregation at 50% of Max. Aggregation |
|---|---|
| 0 | 0 |
| 50 μl. | 1.1 min. |
| 200 μl. | 2.0 min. |

The method of procedure 7 may also be used to measure the titer of KLH-PGH$_2$ mimic antibodies.

Radioimmunoassay Procedure

The antibodies raised against PGE-type mimics and PGX mimics can be used in an RIA for PGE-type compounds of formula I or PGX, respectively. In the following procedures, sensitivity of 6 pg. is sufficient to permit use of antiserum for RIAs, where sensitivity is defined as the amount of authentic PG required to reduce the percent binding from 100% maximum to 80% maximum.

Procedure 8: PGE-type Compound RIA

A known amount of PGE-type compound in 0.1 ml. PBSG buffer at pH 7.4±0.2 and 0.1 ml. of the radiolabeled form of the same PGE-type compound (10,000 cpm/0.1 ml. PBSG) are introduced into a 12×75 mm. polypropylene tube. Antiserum (0.1 ml.) against the corresponding mimic is added at a dilution which will bind 50%±3% of the radiolabeled authentic PGE-type compound in the absence of competition from the unlabeled PGE-type compound. The tube is incubated for 1 hour at 25° and then 12-16 hours at 4°. Antibody bound and free fractions are separated with dextrancoated charcoal. Other separation techniques are acceptable.

If the assay is then run with an unknown and the results compared with those obtained from the known sample, quantitative and qualitative determinations can be made. For example, if the mimic antiserum and [$^3$H] PGE$_2$ are incubated with a sample according to the procedure described, and the [$^3$H] PGE$_2$ is displaced from the antibody, the sample shows qualitative evidence of containing PGE compounds, either PGE$_1$, or PGE$_2$, or both. The quantitative assessment of the amount of PGE compounds present is made by comparing the percent of displaced [$^3$H] PGE$_2$ in the sample with the percent of displaced [$^3$H] PGE$_2$ in a set of standards.

If chromatographic steps are incorporated in the sample processing to separate PGE-type compounds from other classes of prostaglandin, and if the mimic antiserum and [$^3$H] PGE$_2$ are incubated with a sample according to the procedure described, and the [$^3$H] PGE$_2$ is displaced from the antibody, the qualitative evidence that the sample contains PGE compounds is strengthened. The chromatographic steps are similar or equivalent to those described in Christensen and Leyssac, Prostaglandins, 11, 339-420 (1976) and Dray, et al., Europ. J. Clin. Invest. 5, 311-318 (1975).

The data below show the cross-reactivity of antiserum raised against 9-deoxy-9-methylene PGF$_2$ to various PGE-type compounds, relative to PGE$_2$. Percent cross-reaction is defined as (ng. of PGE$_2$ required to displace 50% of [$^3$H] PGE$_2$)/(ng. heterologous PG required to displace 50% of [$^3$H] PGE$_2$)×100.

| COMPOUND | % Cross-Reaction | |
|---|---|---|
| | KLH Conjugate | BSA Conjugate |
| 9-deoxy-9-methylene PGF$_2$ | 100 | 100 |
| PGE$_1$ | 90 | 100 |
| PGA$_1$ | 0.08 | 4.9 |
| PGA$_2$ | 0.75 | 2.8 |
| PGB$_1$ | 0.005 | 0.1 |
| PGB$_2$ | 0.009 | 0.0 |
| 13,14-dihydro-PGE$_2$ | 1.6 | 3.6 |
| 15-keto-PGE$_2$ | 0.03 | 2.5 |
| 13,14-dihydro-15-keto-PGE$_2$ | 0.03 | 0.2 |
| PGD$_1$ | 0.02 | 4.9 |
| PGD$_2$ | 0.02 | 10.0 |
| PGE$_1\alpha$ | 0.09 | 2.9 |
| PGF$_1\beta$ | 0.30 | 5.0 |
| PGF$_2\alpha$ | 0.20 | 1.5 |
| PGF$_2\beta$ | 3.0 | 4.4 |
| 13,14-dihydro-PGF$_2\alpha$ | 0.34 | 0.2 |
| 15-keto-PGF$_2\alpha$ | 0.01 | 0.2 |
| 13,14-dihydro-15-keto-PGF$_2\alpha$ | 0.10 | 0.01 |
| 6-keto-PGF$_1\alpha$ | 0.10 | 0.50 |

Procedure 9: PGX RIA

A known amount of PGX in 0.1 ml. PBSG buffer at pH 8.4±0.3 and 0.1 ml. of radiolabeled PGX (10,000 cpm/0.1 ml PBSG) are introduced into a 12×75 mm polypropylene tube. Antiserum (0.1 ml.) against 9-deoxy-6,9α-epoxy-PGF$_1\alpha$ is added at a dilution which will restore platelet aggregation (2.0 ml. PRP; 1000 μg. arachidonic acid) blocked by 0.050 μg. of PGX in <10 minutes when 50 μl. of antiserum is added. The tube is incubated and the fractions are separated as in procedure 8. The assay is then run with an unknown and the results compared with those obtained from the known sample.

I claim:

1. A conjugate formed by attaching to a carrier molecule which is a macromolecular immunogen of molecular weight greater than 2000 and less than 500,000, a compound selected from the group

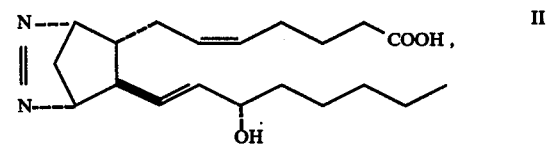

II

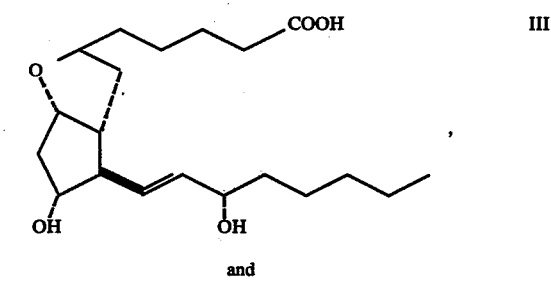

III

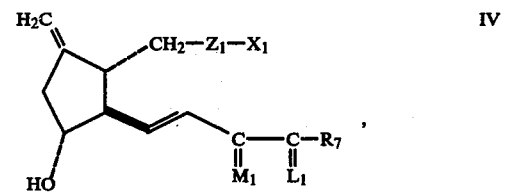

IV wherein M$_1$ is

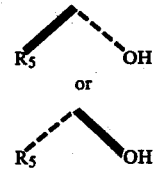

wherein R$_5$ is hydrogen or methyl; wherein L$_1$ is

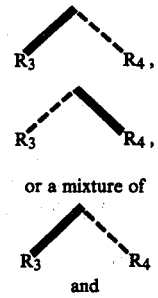

or a mixture of and

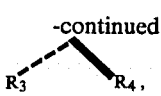

wherein R₃ and R₄ are hydrogen, methyl, or fluoro, being the same or different, with the proviso that one of R₃ and R₄ is fluoro only when the other is hydrogen or fluoro;

wherein Z₁ is
(1) cis—CH=CH—CH₂—(CH₂)$_g$—CH₂—,
(2) cis—CH=CH—CH₂—(CH₂)$_g$—CF₂—,
(3) cis—CH₂—CH=CH—(CH₂)$_g$—CH₂—,
(4) —(CH₂)₃—(CH₂)$_g$—CH₂—,
(5) —(CH₂)₃—(CH₂)$_g$—CF₂—,
(6) —CH₂—O—CH₂—(CH₂)$_g$—CH₂—,
(7) —C≡C—CH₂—(CH₂)$_g$—CH₂—,
(8) —CH₂—C≡C—(CH₂)$_g$—CH₂—,

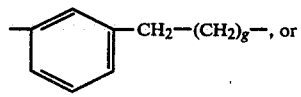 (9)

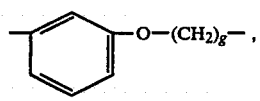 (10)

wherein g is one, 2, or 3;
wherein R₇ is
—(CH₂)$_m$—CH₃, (1)

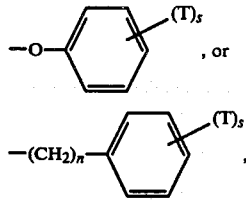 (2) (3)

wherein m is one to 5, inclusive; n is zero or one; T is chloro, fluoro, trifluoromethyl, alkyl of one to 3 carbon atoms, inclusive, or alkoxy of one to 3 carbon atoms, inclusive; and s is zero, one, 2, or 3, the various T's being the same or different, with the proviso that not more than two T's are other than alkyl, with the further proviso that R₇ is

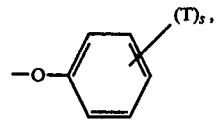

wherein T and s are as defined above, only when R₃ and R₄ are hydrogen or methyl, being the same or different; and wherein X₁ is —COOR₁ wherein R₁ is hydrogen or a pharmacologically acceptable cation.

2. The conjugate of claim 1 where the carrier molecule is selected from the group natural protein, synthetic polypeptide, and other immunogen of molecular weight greater than 2500.

3. The conjugate of claim 2 where the carrier molecule is selected from the group mammal or bird albumin, mammal or bird globulin, poly-1-lysine, and polypeptide of molecular weight greater than 2500.

4. The conjugate of claim 3 where the carrier molecule is selected from the group keyhole limpet hemocyanin and bovine serum albumin.

5. The conjugate of claim 1 when formed in the presence of a coupling agent selected from the group carbonyl diimidazole, alkylchloroformate where the alkyl is of one through eight carbon atoms, and water soluble carbodiimide.

6. The conjugate of claim 5 when the coupling agent is 1-ethyl-3-(3-dimethylaminopropyl)carbodiimide.

7. The conjugate of claim 1 where the PG mimic is a compound of formula IV.

8. The conjugate of claim 7 where the PG mimic is a 9-deoxy-9-methylene-PGF₁-type compound.

9. The conjugate of claim 7 where the PG mimic is a 9-deoxy-9-methylene-PGF₂-type compound.

10. The conjugate of claim 7 where the PG mimic is a compound of the formula

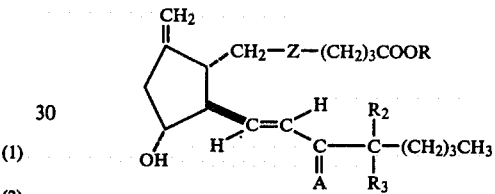 V wherein Z is —CH₂CH₂— or cis—CH=CH—; wherein R is hydrogen or a pharmacologically acceptable cation; wherein R₂ and R₃ are hydrogen, methyl, or ethyl; and wherein A is

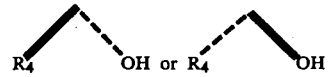

wherein R₄ is hydrogen, methyl, or ethyl with the proviso that R₂ and R₃ are both hydrogen when R₄ is methyl or ethyl.

11. The conjugate of claim 10 where the PG mimic is a 9-deoxy-9-methylene PGF₁-type compound.

12. The conjugate of claim 11 where the PG mimic is 9-deoxy-9-methylene PGF₁.

13. The conjugate of claim 10 where the PG mimic is a 9-deoxy-9-methylene-PGF₂-type compound.

14. The conjugate of claim 13 where the PG mimic is 9-deoxy-9-methylene-PGF₂.

15. The conjugate of claim 13 where the PG mimic is 9-deoxy-9-methylene-15(R)-15-methyl-PGF₂.

16. The conjugate of claim 13 where the PG mimic is 9-deoxy-9-methylene-15(S)-15-methyl-PGF₂.

17. The conjugate of claim 1 where the PG mimic is (5Z,9α,11α,13E,15S)-9,11-azo-15-hydroxyprosta-5,13-dien-1-oic acid.

18. The conjugate of claim 1 where the PG mimic is 9-deoxy-6,9α-epoxy-PGF₁α.

* * * * *